(12) United States Patent
Yokobayashi

(10) Patent No.: US 10,081,448 B2
(45) Date of Patent: Sep. 25, 2018

(54) CONTAINER STERILIZATION METHOD AND CONTAINER STERILIZATION EQUIPMENT

(71) Applicant: Hitachi Zosen Corporation, Osaka-shi, Osaka (JP)

(72) Inventor: Takayasu Yokobayashi, Osaka (JP)

(73) Assignee: Hitachi Zosen Corporation, Osaka-shi, Osaka (JP)

( * ) Notice: Subject to any disclaimer, the term of this patent is extended or adjusted under 35 U.S.C. 154(b) by 61 days.

(21) Appl. No.: 15/025,376

(22) PCT Filed: Jul. 9, 2014

(86) PCT No.: PCT/JP2014/068248
§ 371 (c)(1),
(2) Date: Mar. 28, 2016

(87) PCT Pub. No.: WO2015/059960
PCT Pub. Date: Apr. 30, 2015

(65) Prior Publication Data
US 2016/0229572 A1 Aug. 11, 2016

(30) Foreign Application Priority Data

Oct. 24, 2013 (JP) .................................. 2013-220695

(51) Int. Cl.
*B65B 55/08* (2006.01)
*A61L 2/08* (2006.01)
*G21K 5/02* (2006.01)

(52) U.S. Cl.
CPC .............. *B65B 55/08* (2013.01); *A61L 2/087* (2013.01); *G21K 5/02* (2013.01); *A61L 2202/14* (2013.01); *A61L 2202/23* (2013.01)

(58) Field of Classification Search
CPC ............ B65B 55/08; G21K 5/02; A61L 2/087
See application file for complete search history.

(56) References Cited

U.S. PATENT DOCUMENTS 8,293,173 B2 * 10/2012 Bufano ................... A61L 2/087
250/492.1
8,636,949 B2 * 1/2014 Bufano ................... A61L 2/087
250/492.3
(Continued)

FOREIGN PATENT DOCUMENTS

CN  101062425 A  10/2007  ............... A61L 2/08
CN  101626957 A  1/2010  ............. B65B 55/08
(Continued)

OTHER PUBLICATIONS

Office Action issued in corresponding Chinese Patent Application No. 201480053452.4 dated Sep. 28, 2016.
(Continued)

*Primary Examiner* — Regina M Yoo
(74) *Attorney, Agent, or Firm* — Kusner & Jaffe

(57) ABSTRACT

Electron beams are irradiated to substantially identical sterilization surfaces on a container from a first upstream electron-beam irradiating device and a first downstream electron-beam irradiating device that are spaced with a predetermined distance upstream and downstream on a container carrier path. A sterilization controller controls the sum of electron beam outputs irradiated from the upstream electron-beam irradiating device and the downstream electron-beam irradiating device so as to allow sterilization on the sterilization surfaces of the container.

6 Claims, 6 Drawing Sheets

(56) References Cited

U.S. PATENT DOCUMENTS

| | | | |
|---|---|---|---|
| 9,656,812 B2* | 5/2017 | Voth | B65G 35/06 |
| 2002/0114728 A1 | 8/2002 | Kulish et al. | 422/22 |
| 2003/0039579 A1* | 2/2003 | Lambert | A61L 2/087 |
| | | | 422/22 |
| 2006/0151714 A1 | 7/2006 | Thilly et al. | 250/453.11 |
| 2007/0253861 A1 | 11/2007 | Naka et al. | 422/22 |
| 2010/0140507 A1 | 6/2010 | Nishino et al. | 250/491.1 |
| 2011/0012030 A1* | 1/2011 | Bufano | A61L 2/087 |
| | | | 250/492.3 |
| 2011/0012032 A1* | 1/2011 | Bufano | A61L 2/087 |
| | | | 250/492.3 |
| 2011/0101248 A1 | 5/2011 | Nishino et al. | 250/492.3 |
| 2012/0145929 A1 | 6/2012 | Nishino et al. | 250/492.3 |
| 2013/0202481 A1 | 8/2013 | Kobayashi et al. | 422/22 |
| 2014/0231673 A1 | 8/2014 | Yokobayashi et al. | 250/455.11 |
| 2014/0299786 A1 | 10/2014 | Yokobayashi et al. | 250/455.11 |
| 2014/0369885 A1 | 12/2014 | Krueger | 422/22 |

FOREIGN PATENT DOCUMENTS

| | | | | |
|---|---|---|---|---|
| CN | 101797986 A | 8/2010 | | A61L 2/08 |
| CN | 102526778 A | 7/2012 | | A61L 2/08 |
| JP | 57-37875 | 8/1982 | | H01J 37/04 |
| JP | 61-257172 | 11/1986 | | A23L 3/26 |
| JP | 2006-518689 | 8/2006 | | B65B 55/08 |
| JP | 3952708 | 8/2007 | | G21K 5/04 |
| JP | 2008-239181 | 10/2008 | | B65B 55/08 |
| JP | 2011-93567 | 5/2011 | | A23L 3/26 |
| JP | 2012-066847 | 4/2012 | | B65B 55/08 |
| JP | 2013-086822 A | 5/2013 | | A61L 2/08 |
| JP | 2013-088225 A | 5/2013 | | A61L 2/10 |
| WO | WO 2002/061464 A1 | 8/2002 | | G01V 5/00 |
| WO | WO 2011/011079 A1 | 1/2011 | | A61L 2/08 |
| WO | WO 2013/092735 A1 | 6/2013 | | A61L 2/08 |
| WO | WO 2014/086675 A2 | 6/2014 | | G01T 1/29 |

OTHER PUBLICATIONS

Supplementary Partial European Search Report issued in corresponding European Patent Application No. 14 85 5158 dated Jun. 7, 2017.

International Search Report from corresponding International Patent Application No. PCT/JP2014/068248, dated Oct. 21, 2014.

* cited by examiner

CONTAINER STERILIZATION METHOD AND CONTAINER STERILIZATION EQUIPMENT

TECHNICAL FIELD

The present invention relates to a container sterilization method and container sterilization equipment in which a plurality of electron-beam irradiating devices are provided in parallel along a container conveyance path.

BACKGROUND ART

The container sterilization equipment includes two heads that irradiate an object to be treated with electron beams and two filament power supplies that supply power to the filaments of the two heads. Each of the filament power supplies for the respective heads has a switch that compares a beam depletion threshold value estimated according to the magnitude of a beam control signal with an actual beam current measured value. When the beam current measured value is not higher than the beam depletion threshold value, it is decided that beams are depleted. This stops power supply to the filament of the beam-depleted head while keeping filament power to other heads.

Thus, in an electron-beam irradiating device with power sharing multiple beam heads, discharge from one head stops only an abnormal head but keeps beams to other heads. This eliminates the need for stopping the operations of all the heads.

CITATION LIST

Patent Literature

Patent Literature 1: Japanese Patent No. 3952708

SUMMARY OF INVENTION

Technical Problem

For example, electron beam sterilization equipment that sterilizes a container by irradiation of electron beams can sterilize about 600 containers per minute and is interlocked with a filling device provided downstream of the equipment. If an electron-beam irradiating device requires replacement of an electron beam emitter because of an accident or deterioration, the electron beam sterilization equipment needs to be stopped for a sufficient time period.

Moreover, each container is irradiated with electron beams for 0.1 seconds. If sparking occurs on the electron-beam irradiating device, it takes about 0.1 to 0.2 seconds to recover the original irradiation output. Thus, a container passing through the sparked electron-beam irradiating device may directly contaminate a sterilizing chamber or the filling device that is equipment downstream of the electron-beam irradiating device. In this case, the overall equipment needs to be stopped to be cleaned.

Thus, in electron-beam container sterilization equipment for high-speed sterilization, it is important to operate an electron-beam irradiating device with minimum spark and prevent an unsterilized container from being transported and contaminating downstream equipment in the event of sparking.

An object of the present invention is to provide a container sterilization method and container sterilization equipment which can continuously operate an electron-beam irradiating device by shortening the stop time of the device, prevent an unsterilized container from contaminating a downstream device even if sparking temporarily reduces an electron beam output, and suppress the occurrence of sparking.

Solution to Problem

A container sterilization method according to a first aspect for sterilizing a container with electron beams irradiated from electron-beam irradiating devices while transporting the container along a carrier path, the method including:

irradiating substantially identical outside surface of the container with electron beams irradiated from one or more upstream electron-beam irradiating device and one or more downstream electron-beam irradiating device spaced to each other with a predetermined distance along the carrier path; and controlling a sum of electron beam outputs irradiated from the upstream and downstream electron-beam irradiating devices by means of a sterilization controller so as to at least allow sterilization on the surface of the container.

A container sterilization method according to a second aspect, in the method of the first aspect, when the electron beam output irradiated from the upstream electron-beam irradiating device changes from a set range, changing the electron beam output irradiated from the downstream electron-beam irradiating device so as to control the sum of the electron beam outputs from the upstream and downstream electron-beam irradiating devices to be equal to or higher than the set range of an electron beam output that allows external sterilization on the container when the container irradiated with the changed electron-beam output at the upstream electron-beam irradiating device is transported to the downstream electron-beam irradiating device.

A container sterilization method according to a third aspect, in the method of the first or second aspect, wherein each of the electron-beam irradiating device has a vacuum chamber, the method further including: monitoring a vacuum state in the vacuum chamber of each of the electron-beam irradiating devices; and controlling an electron beam output of the electron-beam irradiating device including the vacuum chamber with a low degree of vacuum to be smaller than an electron beam output of the electron-beam irradiating device including the vacuum chamber with a high degree of vacuum in order to prevent sparking in the electron-beam irradiating device including the vacuum chamber with the low degree of vacuum.

Container sterilization equipment according to a fourth aspect for externally sterilizing a container with electron beams irradiated from electron-beam irradiating devices facing a carrier path while transporting the container along the carrier path, including one or more upstream electron-beam irradiating device and one or more downstream electron-beam irradiating device spaced to each other with a predetermined distance along the carrier path for irradiating substantially identical surface of the container with electron beams, and a sterilization controller for controlling a sum of electron beam outputs irradiated from the upstream electron-beam irradiating device and the downstream electron-beam irradiating device so as to allow sterilization on the surface of the container, wherein the sterilization controller controls such that, when the electron beam output from the upstream electron-beam irradiating device changes from a set range, the container irradiated from the upstream electron-beam irradiating device with the electron beam is transported so as to face the downstream electron-beam irradiating device, and an electron beam output from the downstream electron-beam irradiating device is controlled to change the sum of the upstream electron beam output and the downstream electron beam output so as to at least allow external sterilization on the container.

Container sterilization equipment according to a fifth aspect, in the configuration of the fourth aspect, further including a rejecting device provided downstream of the downstream electron beam sterilization equipment on the carrier path so as to eject the container on the carrier path, the sterilization controller operating the rejecting device so as to eject, from the carrier path, the container with a changed electron beam output irradiated from the upstream electron-beam irradiating device.

Container sterilization equipment according to a sixth aspect externally sterilizes a container with electron beams irradiated from electron-beam irradiating devices having a vacuum chamber and facing a carrier path while transporting the container along the carrier path, wherein the electron-beam irradiating devices includes one or more upstream electron-beam irradiating device and one or more downstream electron-beam irradiating device spaced to each other with a predetermined distance along the carrier path, the upstream and downstream electron-beam irradiating devices irradiating substantially identical sterilization surface of the container with electron beams, the electron-beam irradiating device includes a vacuum chamber, the container sterilization equipment includes a vacuum sensor for detecting a degree of vacuum in the vacuum chamber and a sterilization controller, and the sterilization controller controls an electron beam output of the electron-beam irradiating device including the vacuum chamber with a low degree of vacuum such that the electron beam output thereof is smaller than an electron beam output of the electron-beam irradiating device including the vacuum chamber with a high degree of vacuum; meanwhile, the sterilization controller controls a sum of electron beam outputs irradiated from the upstream electron-beam irradiating device and the downstream electron-beam irradiating device so as to allow sterilization on the surface of the container.

Advantageous Effects of Invention

According to the invention of the first aspect, the electron-beam irradiating devices sterilize the substantially identical surfaces of the container with electron beams. Thus, if the electron beam irradiation dose of the electron-beam irradiating device is reduced by a failure, maintenance, deterioration caused by an extended operating time, or secular change, the maintained electron beam output of the other not reduced electron-beam irradiating device can be increased by the sterilization controller. This can eliminate a stop time and enables a continuous operation.

According to the configuration of the second aspect, if an electron dose irradiated upstream to the container is reduced below a set amount because of sparking or the like, the downstream electron-beam irradiating device increases an electron dose irradiated to the container, thereby externally sterilizing the container with reliability. This prevents an insufficiently sterilized container from being transported to downstream equipment, eliminating contamination of the downstream equipment. This may less frequently stop the sterilization equipment, leading to a longer operating time.

According to the invention of the third aspect, a vacuum state is monitored in the vacuum chamber of the electron-beam irradiating device, allowing the electron-beam irradiating device having a low degree of vacuum to operate with a reduced electron beam output. This can prevent sparking that is likely to occur in the electron-beam irradiating device having a low degree of vacuum, thereby suppressing the occurrence of insufficiently sterilized containers.

According to the configuration of the fourth aspect, the electron-beam irradiating devices that sterilize the substantially identical surfaces of the container are spaced with the predetermined distance on the conveyance path. The electron beam output of the electron-beam irradiating device with an electron beam irradiation dose reduced by a failure, maintenance, deterioration, or secular change is adjusted to as to enable an extended continuous operation. In the event of an accident that may reduce the electron beam output of the electron-beam irradiating device or stop the electron-beam irradiating device, the electron beam output of the other electron-beam irradiating device is increased so as to continue an extended operation without stopping the sterilization equipment. This can flexibly respond to the accident.

According to the invention of the fifth aspect, the container with a changed electron beam output may be deteriorated in quality by excessive irradiation of electron beams. Such a container is ejected as an insufficiently sterilized container from the conveyance path by the rejecting device, preferably achieving continuous sterilization of containers.

According to the invention of the sixth aspect, a vacuum state of the vacuum chamber is monitored by the vacuum sensor in the electron-beam irradiating devices that are spaced with the predetermined distance on the conveyance path, and the sterilization controller reduces the electron beam output of the electron-beam irradiating device including the vacuum chamber with a low degree of vacuum and increases the electron beam output of the electron-beam irradiating device including the vacuum chamber with a high degree of vacuum. This controls the sum of the electron beam outputs of the upstream electron-beam irradiating device and the downstream electron-beam irradiating device so as to allow sterilization on the sterilization surfaces of the container, thereby preventing the occurrence of sparking in the electron-beam irradiating device with a low degree of vacuum and considerably reducing the occurrence of insufficiently sterilized containers.

DESCRIPTION OF EMBODIMENTS

First Embodiment

Referring to FIGS. 1 to 5, a first embodiment of electron-beam container sterilization equipment according to the present invention will be described below.
(Equipment Overview)

Figure 1:
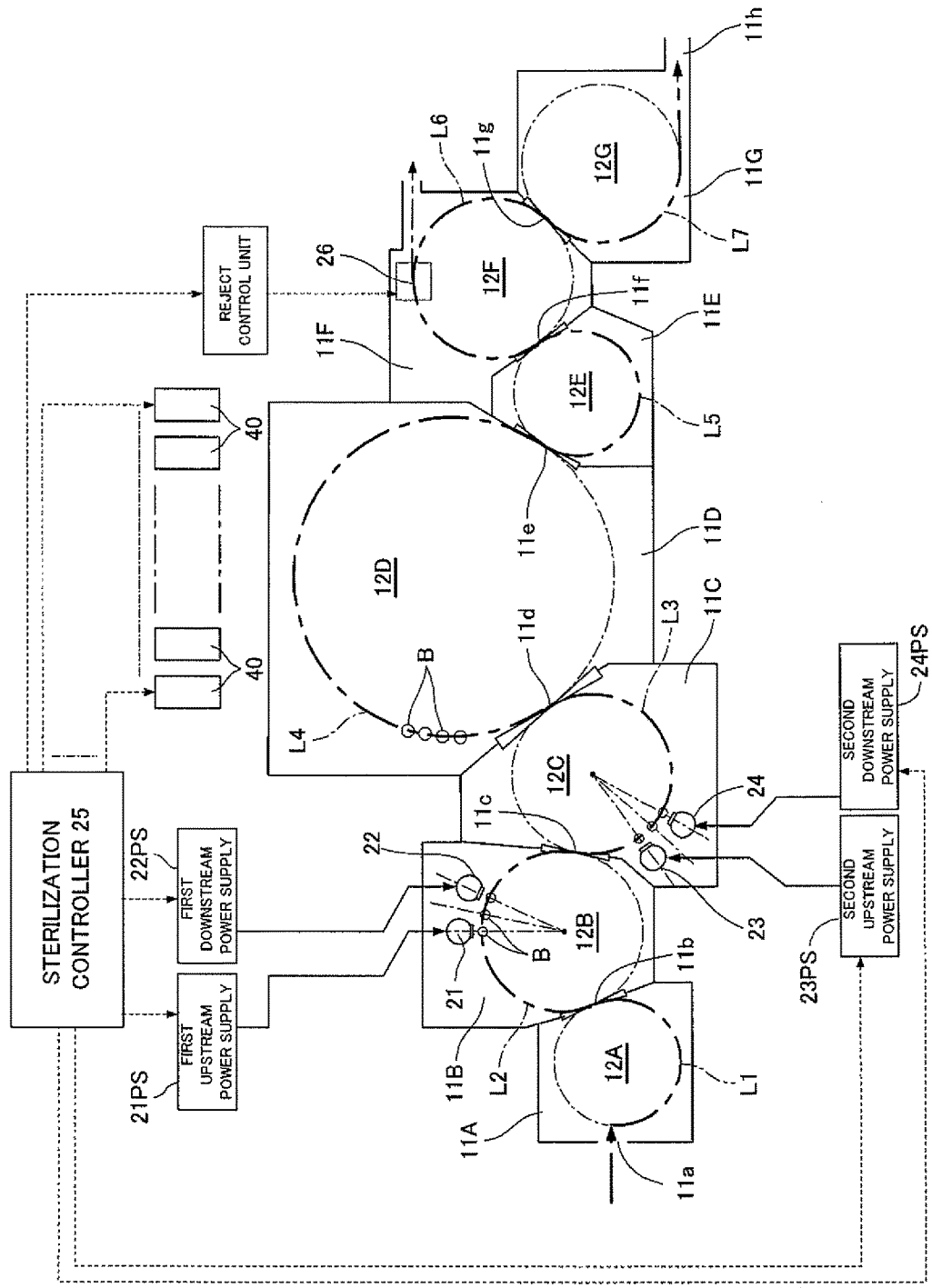
FIG. 1 is a schematic plan view showing a first embodiment of container sterilization equipment according to the present invention.

As shown in FIG. 1, a plurality of first to seventh shielded chambers 11A to 11G are connected in series via container entrances/exits 11a to 11h. The first to seventh shielded chambers 11A to 11G contain first to seventh container carrier devices 12A to 12G that transport containers B at regular intervals P.

The first shielded chamber 11A on the entrance side has a circular container carrier path L1 along which the first container carrier device 12A transports the containers B. The first shielded chamber 11A prevents leakage of electron beams (X-rays) to the container entrance 11a.

The second shielded chamber 11B and the third shielded chamber 11C are external sterilization chambers that sterilize the outer surfaces of the containers B. In the second shielded chamber 11B, a first upstream electron-beam irradiating device 21 and a first downstream electron-beam irradiating device 22 are spaced with a certain distance (e.g., twice as large as the interval P) on the outer periphery of a container carrier path L2 formed by the second container carrier device 12B. In the third shielded chamber 11C, a second upstream electron-beam irradiating device 23 and a second downstream electron-beam irradiating device 24 are spaced with a certain distance (twice as large as the interval P) on the outer periphery of a container carrier path L3.

The fourth shielded chamber 11D is an internal sterilization chamber that sterilizes the inner surfaces of the containers B. Along the upper part of a circular fourth container carrier path L4 where the containers B are transported by the fourth container carrier device 12D, a plurality of internal electron-beam irradiating devices (not shown) shaped like nozzles insertable into the containers B from the openings of the containers B are paired with internal sterilization power supplies so as to be spaced at regular intervals.

The fifth to seventh shielded chambers 11E to 11G are exit-side shielded chambers that prevent leakage of electron beams (X-rays) from the container exit 11h. Circular carrier paths L5 to L7 are formed along which the fifth to seventh container carrier devices 12E to 12G transport the containers B. The intermediate sixth shielded chamber 11F contains a rejecting device 26 that ejects the insufficiently sterilized containers B from the circular carrier path L6.
(Container Carrier Device)

Figure 3:
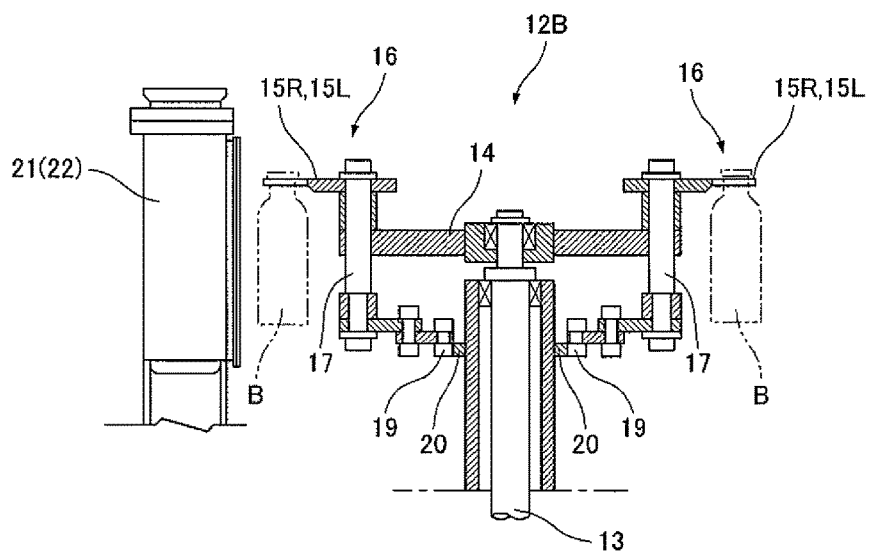
FIG. 3 is a longitudinal section of a container carrier device.
Figure 4:
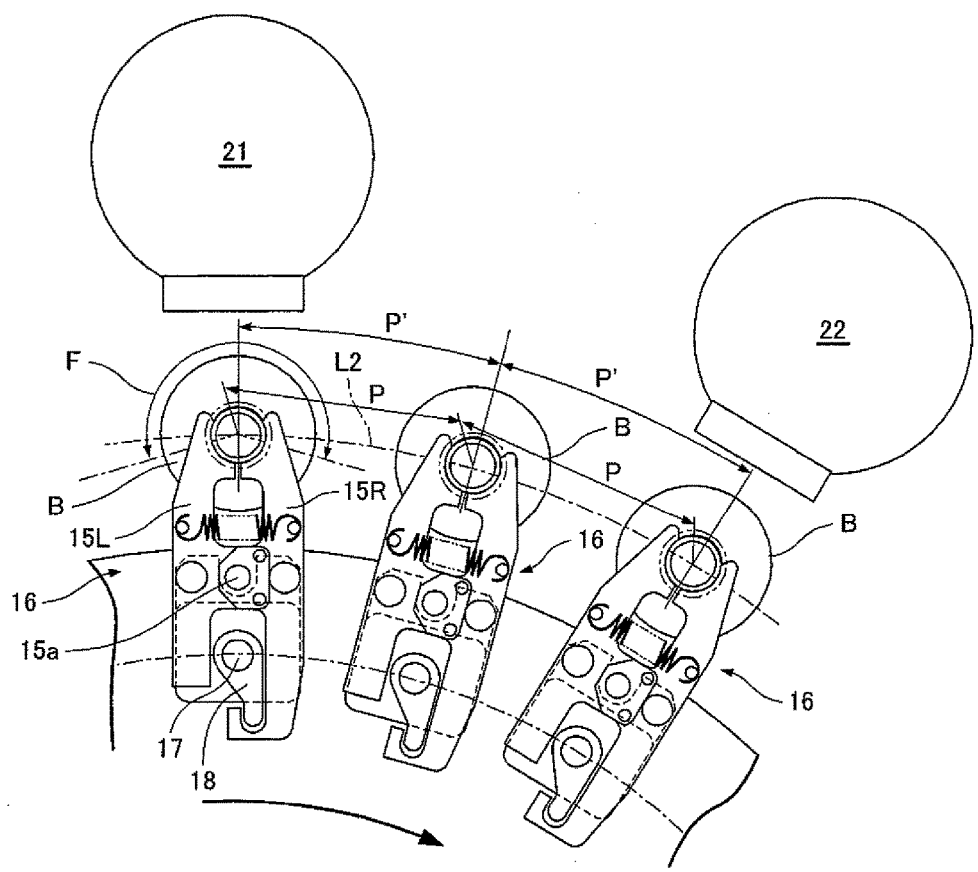
FIG. 4 is a plan view of first electron-beam irradiating devices.

For example, as shown in FIGS. 3 and 4, the second container carrier device 12B includes a turning table 14 rotatably supported by a main shaft 13 raised on a pedestal and container holding devices 16 that are provided at the regular intervals P on the outer periphery of the turning table 14 so as to hold the necks of the containers B with pairs of holding arms 15R and 15L. Reference numeral 17 denotes a pivot shaft that pivotally penetrates the turning table 14. An arm open/close cam 18 is attached to the upper end of the pivot shaft 17 so as to open the holding arms 15R and 15L restrained with a spring in a closing direction. An open/close cam follower 20 is attached to the lower end of the pivot shaft 17 via an arm member so as to follow a holding open/close cam 19 fixed below the turning table 14.

The second container carrier device 12B was described above. The first, third, and fifth to seventh container carrier devices 12A, 12C, and 12E to 12G other than the fourth container carrier device 12D are substantially identical in configuration to the second container carrier device 12B. The fourth container carrier device 12D has an elevating mechanism (not shown) that relatively moves up and down the containers B held by the container holding devices 16 and the internal electron-beam irradiating devices shaped like nozzles, inserting the internal electron-beam irradiating devices from the openings of the containers B.
(Electron-Beam Irradiating Device)

Figure 2:
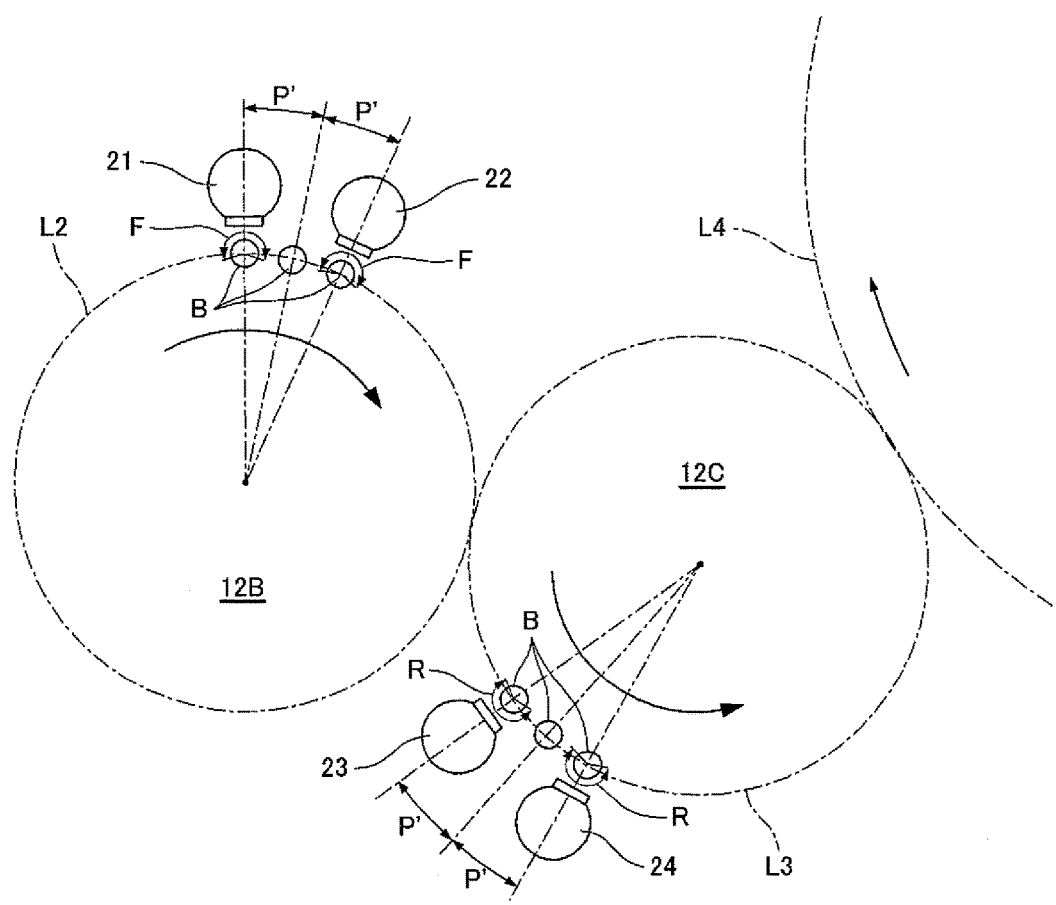
FIG. 2 is an enlarged plan view for explaining the layout of external electron-beam irradiating devices.

As shown in FIG. 2, the second shielded chamber 11B contains a first upstream electron-beam irradiating device 21 and a first downstream electron-beam irradiating device 22 that irradiate sterilization surfaces F on the containers B with electron beams. The electron-beam irradiating devices 21 and 22 are spaced with, for example, a distance P' twice as large as the interval P upstream and downstream on the outer periphery of the carrier path L2. The third shielded chamber 11C contains a second upstream electron-beam irradiating device 23 and a second downstream electron-beam irradiating device 24 that irradiate external sterilization surfaces R on the containers B with electron beams. The electron-beam irradiating devices 23 and 24 are spaced with, for example, the distance P' twice as large as the interval P upstream and downstream on the outer periphery of the carrier path L3. In this configuration, the sterilization surfaces F and R are irradiated with electrons at angles larger than 90° with respect to the irradiation direction of electron beams because of the irradiation characteristics of electron beams.

The electron-beam irradiating devices 21 to 24 include a first upstream power supply 21PS, a first downstream power supply 22PS, a second upstream power supply 23PS, and a second downstream power supply 24PS, respectively, that supply predetermined power for generating electron beams. A sterilization controller 25 controls the power supplies 21PS, 22PS, 23PS, and 24PS so as to control the outputs of electron beams irradiated from the electron-beam irradiating devices 21 to 24. Moreover, the sterilization controller 25 controls the rejecting device 26 of the sixth shielded chamber 11F.

Figure 5:
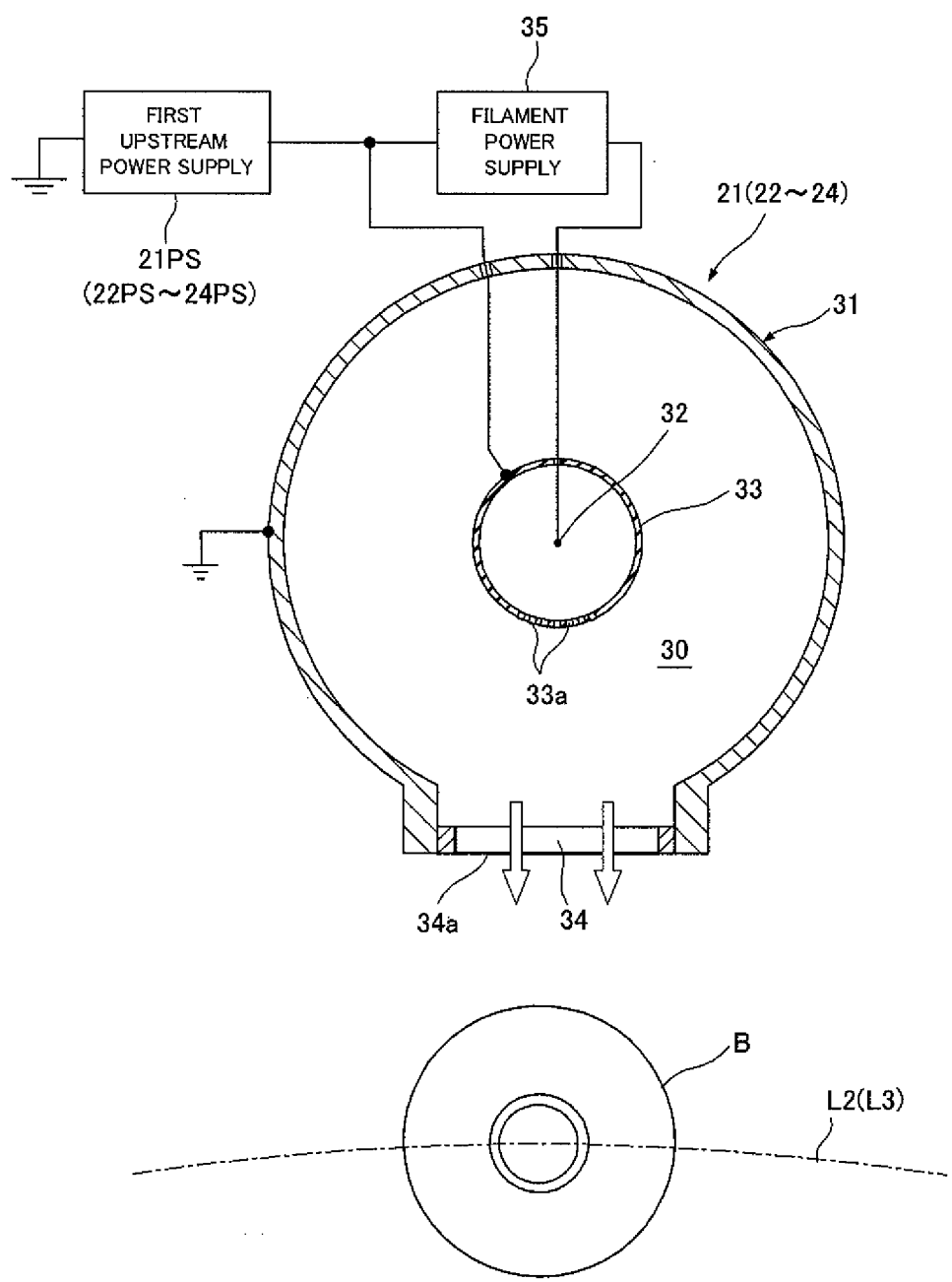
FIG. 5 is a cross-sectional view of the external electron-beam irradiating device.

As shown in FIG. 5, each of the electron-beam irradiating devices 21 to 24 has a cylindrical housing 31 in a vertical position. The housing 31 has an irradiation hole 34 having a predetermined position formed at a predetermined height on the side of the housing 31. A metallic thin film 34a is attached to the irradiation hole 34 so as to seal a vacuum chamber 30 in a vacuum in the housing 31. A filament 32 is placed in the housing 31 and an electrode 33 having transparent windows 33a formed is provided around the filament 32. Power is supplied from the first upstream power supply 21PS (22PS to 24PS) to the electrodes 33 and then is supplied to the filament 32 through a filament power supply 35. This generates electron beams between the filament 32 and the electrode 33. Electron beams are irradiated from the transparent windows 33a to the containers B through the vacuum chamber 30 and the irradiation hole 34.

The vacuum chambers 30 of the electron-beam irradiating devices 21 to 24 has a first upstream vacuum sensor 21VS, a first downstream vacuum sensor 22VS, a second upstream vacuum sensor 23VS, and a second downstream vacuum sensor 24VS, respectively, that detect a vacuum state. Degrees of vacuum in the vacuum chambers 30 are inputted to the sterilization controller 25 by the vacuum sensors 21VS to 24VS.

In this configuration, the first electron-beam irradiating devices 21 and 22 of the second shielded chamber 11B and the second electron-beam irradiating devices 23 and 24 of the third shielded chamber 11C are substantially identical in configuration except for irradiation of electron beams for sterilizing the substantially half sterilization surfaces F and R that are symmetrical to each other on the container B. Thus, only the first electron-beam irradiating devices 21 and 22 of the second shielded chamber 11B will be described below and the explanation of the second electron-beam irradiating devices 23 and 24 of the third shielded chamber 11C is omitted.

Based on the degree of vacuum of the vacuum chamber 30 in each of the first electron-beam irradiating devices 21 and 22, the sterilization controller 25 is set so as to reduce the electron beam output of the electron-beam irradiating device (e.g., 21) including the vacuum chamber 30 with a low degree of vacuum and increase the electron beam output of the electron-beam irradiating device 22 including an electron beam generator with a high degree of vacuum. This is because a decrease in the degree of vacuum of the vacuum chamber 30 is likely to cause sparking between the electrode 33 and the housing 31 grounded in the electron-beam irradiating device 21 (22 to 24), temporarily (for 0.1 to 0.2 seconds) stopping outputting electron beams. This may reduce an electron dose irradiated to the sterilization surface F of the container B and cause poor sterilization.

Moreover, the sterilization controller 25 controls the sum of electron beam outputs irradiated from the first electron-beam irradiating devices 21 and 22 so as to allow sterilization on the sterilization surface F of the container B.

The sterilization controller 25 can detect the output of electron beams irradiated from the first upstream electron-beam irradiating device 21 to the container B according to a supplied current if the output is changed (reduced) from a set range (threshold) by sparking between the grounded housing 31 and the electrode 33. The occurrence of sparking temporarily (for 0.1 to 0.2 seconds) stops the output of electron beams irradiated from the first upstream electron-beam irradiating device 21. Thus, the sum of electron beam outputs irradiated from the first electron-beam irradiating devices 21 and 22 may be reduced below the set value (threshold) that allows sterilization on the sterilization surface F of the container B. In addition to sparking, the output of electron beams may be stopped if the metallic thin film 34a of the irradiation hole 34 is broken by deterioration of the electron-beam irradiating device.

At this point, the sterilization controller 25 controls the electron beam output of the first downstream electron-beam irradiating device 22 such that after a time period during which the container B is transported to the subsequent irradiation position by two pitches, the electron beam output irradiated to the container B is increased and the sum of the electron beam output of the first downstream electron-beam irradiating device 22 and the electron beam output irradiated by the first upstream electron-beam irradiating device 21 (in a state of a reduced output) is not lower than the lower limit of the set value (threshold) that allows sterilization on the sterilization surface F of the container B.

In this way, the electron beam output irradiated to the sterilization surface F of the container B is large enough to at least allow sterilization on the sterilization surface F, preventing the containers B from passing through being unsterilized. This can prevent the containers B transported to the container carrier paths L3 to L7 from contaminating the interiors of the third to seventh shielded chambers 11C to 11G.

Since the container B with a varying electron beam output may excessively radiate electron beams, the sterilization controller 25 operates the rejecting device 26 of the sixth shielded chamber 11F so as to remove the container B from the container carrier path L6.

In this case, at least the first downstream electron-beam irradiating device 22 can preferably output electron beams so as to allow sterilization on the sterilization surface F of the container B even if the electron beam output of the first upstream electron-beam irradiating device 21 is stopped.

For example, if the sterilization equipment can treat (sterilize) 600 containers B per minute, each of the electron-beam irradiating devices 21 to 24 irradiates the container B with electron beams for 0.1 seconds. The container B is transported in 0.2 seconds from the first and second upstream electron-beam irradiating devices 21 and 23 to the first and second downstream electron-beam irradiating devices 22 and 24. The sterilization controller 25 has to adjust the outputs of the first and second downstream electron-beam irradiating devices 22 and 24 in 0.2 seconds.

In the first embodiment, an electron beam output is set based on a vacuum state in each of the vacuum chambers 30 of the electron-beam irradiating devices 21 to 24. The electron beam outputs of the upstream electron-beam irradiating devices 21 and 23 and the downstream electron-beam irradiating devices 22 and 24 may be set based on the operating times and conditions of the upstream electron-beam irradiating devices 21 and 23 and the downstream electron-beam irradiating devices 22 and 24.

For the sterilization surfaces F and R, the second shielded chamber 11B and the third shielded chamber 11C each include two of the first and second electron-beam irradiating devices 21 to 24. At least three electron-beam irradiating devices may be provided in each of the shielded chambers.

In the first embodiment, the electron beam output is controlled according to a lapse of time. The electron beam output may be controlled by detecting the angle of rotation of the turning table 14 with a detector (e.g., a rotary encoder) and monitoring the position of the container B.

Second Embodiment

Figure 6:
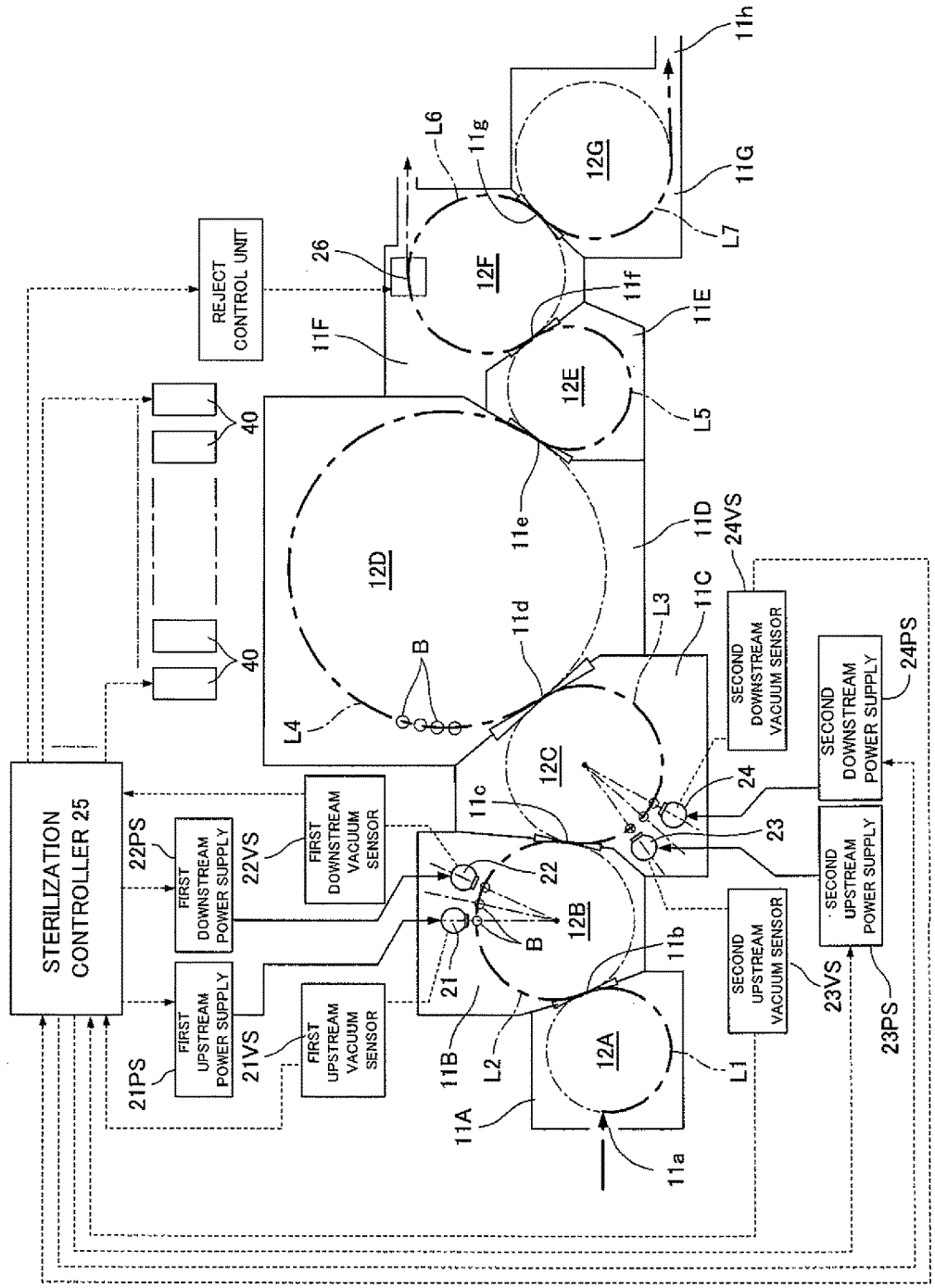
FIG. 6 is a schematic plan view showing a second embodiment of container sterilization equipment according to the present invention.
Figure 7:
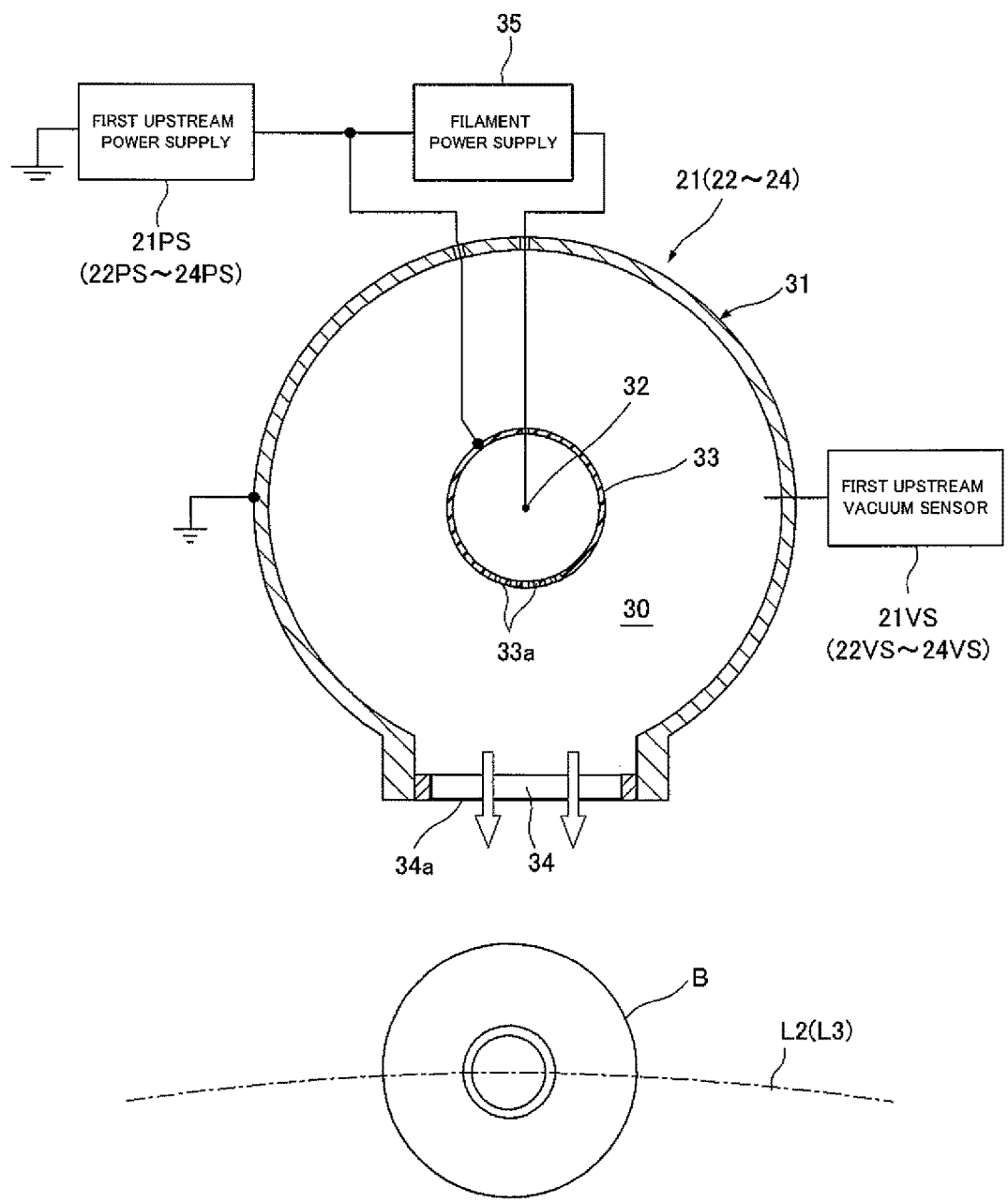
FIG. 7 is a plan sectional view of an external electron-beam irradiating device.

Referring to FIGS. 6 and 7, a second embodiment of electron-beam container sterilization equipment according to the present invention will be described below. An electron-beam irradiating device according to the second embodiment is configured in consideration of sparking that is more likely to occur with a reduction in the degree of vacuum in a vacuum chamber. Vacuum sensors 21VS to 24VS are provided to detect degrees of vacuum in vacuum chambers 30 of electron-beam irradiating devices 21 to 24. The same parts as those of the first embodiment are indicated by the same reference numerals and the explanation thereof is omitted. For example, "Equipment overview" and "container carrier device" are identical in configuration to those of the first embodiment and thus the explanation thereof is omitted. Furthermore, "electron-beam irradiating device" is identical to that of the first embodiment except for the provision of the vacuum sensors. FIGS. 2 to 4 are also identical to the configuration of the present embodiment and thus the explanation thereof is omitted.

As shown in FIG. 1, a plurality of first to seventh shielded chambers 11A to 11G are connected in series via container entrances/exits 11a to 11h. The first to seventh shielded chambers 11A to 11G contain first to seventh container carrier devices 12A to 12G that transport containers B at regular intervals P.

The first shielded chamber 11A on the entrance side has a circular container carrier path L1 formed along which the first container carrier device 12A transports the containers B. The first shielded chamber 11A prevents leakage of electron beams (X-rays) to the container entrance 11a.

The second shielded chamber 11B and the third shielded chamber 11C are external sterilization chambers that sterilize the outer surfaces of the containers B. In the second shielded chamber 11B, a first upstream electron-beam irradiating device 21 and a first downstream electron-beam irradiating device 22 are spaced with a certain distance (twice as large as the interval P) on the outer periphery of a container carrier path L2 formed by the second container carrier device 12B. In the third shielded chamber 11C, a second upstream electron-beam irradiating device 23 and a second downstream electron-beam irradiating device 24 are spaced with a certain distance (twice as large as the interval P) on the outer periphery of a container carrier path L3.

The fourth shielded chamber 11D is an internal sterilization chamber that sterilizes the inner surfaces of the containers B. Along the upper part of a circular fourth container carrier path L4 where the containers B are transported by the fourth container carrier device 12D, a plurality of internal electron-beam irradiating devices (not shown) shaped like nozzles insertable into the containers B from the openings of the containers B are paired with internal sterilization power supplies 30 so as to be spaced at predetermined intervals.

The fifth to seventh shielded chambers 11E to 11G are exit-side shielded chambers that prevent leakage of electron beams (X-rays) from the container exit 11h. Circular carrier paths L5 to L7 are formed along which the fifth to seventh container carrier devices 12E to 12G transport the containers B. The intermediate sixth shielded chamber 11F contains a rejecting device 26 that ejects the insufficiently sterilized containers B from the circular carrier path L6.

(Container Carrier Device)

For example, as shown in FIGS. 3 and 4, the second container carrier device 12B includes a turning table 14 rotatably supported by a main shaft 13 raised on a pedestal and container holding devices 16 that are provided at the regular intervals P on the outer periphery of the turning table 14 so as to hold the necks of the containers B with pairs of holding arms 15R and 15L. Reference numeral 17 denotes a pivot shaft that pivotally penetrates the turning table 14. An arm open/close earn 18 is attached to the upper end of the pivot shaft 17 so as to open the holding arms 15R and 15L restrained with a spring in a closing direction. An open/close cam follower 20 is attached to the lower end of the pivot shaft 17 via an arm member so as to follow a holding open/close cam 19 fixed below the turning table 14.

The second container carrier device 12B was described above. The first, third, and fifth to seventh container carrier devices 12A, 12C, and 12E to 12G other than the fourth container carrier device 12D are substantially identical in configuration to the second container carrier device 12B. The fourth container carrier device 12D has an elevating mechanism (not shown) that relatively moves up and down the containers B held by the container holding devices 16 and the internal electron-beam irradiating devices shaped like nozzles, inserting the internal electron-beam irradiating devices from the openings of the containers B.

(Electron-Beam Irradiating Device)

As shown in FIG. 2, the second shielded chamber 11B contains a first upstream electron-beam irradiating device 21 and a downstream electron-beam irradiating device 22 that irradiate sterilization surfaces F on the containers B with electron beams. The electron-beam irradiating devices 21 and 22 are spaced with, for example, a distance P' twice as large as the interval P upstream and downstream on the outer periphery of the carrier path L2. The third shielded chamber 11C contains a second upstream electron-beam irradiating device 23 and a second downstream electron-beam irradiating device 24 that irradiate sterilization surfaces R on the containers B with electron beams. The electron-beam irradiating devices 23 and 24 are spaced with, for example, the distance P' twice as large as the interval P upstream and downstream on the outer periphery of the carrier path L3. In this configuration, the sterilization surfaces F and R are irradiated with electrons at angles larger than 90° with respect to the irradiation direction of electron beams because of the irradiation characteristics of electron beams.

The electron-beam irradiating devices 21 to 24 include a first upstream power supply 21PS, a first downstream power supply 22PS, a second upstream power supply 23PS, and a second downstream power supply 24PS, respectively, that supply predetermined power for generating electron beams. A sterilization controller 25 controls the power supplies 21PS, 22PS, 23PS, and 24PS so as to control the outputs of electron beams irradiated from the electron-beam irradiating devices 21 to 24. Moreover, the sterilization controller 25 controls the rejecting device 26 of the sixth shielded chamber 11F.

As shown in FIG. 5, each of the electron-beam irradiating devices 21 to 24 has a cylindrical housing 31 in a vertical position. The housing 31 has an irradiation hole 34 having a predetermined position formed at a predetermined height on the side of the housing 31. A metallic thin film 34a is attached to the irradiation hole 34 so as to seal the vacuum chamber 30 in a vacuum in the housing 31. A filament 32 is placed in the housing 31 and an electrode 33 having transparent windows 33a formed is provided around the filament 32. Power is supplied from the first upstream power supply 21PS (22PS to 24PS) to the electrodes 33 and then is supplied to the filament 32 through a filament power supply 35. This generates electron beams between the filament 32 and the electrode 33. Electron beams are irradiated from the transparent windows 33a to the containers B through the vacuum chamber 30 and the irradiation hole 34.

The vacuum chambers 30 of the electron-beam irradiating devices 21 to 24 has a first upstream vacuum sensor 21VS, a first downstream vacuum sensor 22VS, a second upstream vacuum sensor 23VS, and a second downstream vacuum sensor 24VS, respectively, that detect a vacuum state. Degrees of vacuum in the vacuum chambers 30 are inputted to the sterilization controller 25 by the vacuum sensors 21VS to 24VS.

In this configuration, the first electron-beam irradiating devices 21 and 22 of the second shielded chamber 11B and the second electron-beam irradiating devices 23 and 24 of the third shielded chamber 11C are substantially identical in configuration except for irradiation of electron beams for sterilizing the substantially half sterilization surfaces F and R that are symmetrical to each other on the container B. Thus, only the first electron-beam irradiating devices 21 and 22 of the second shielded chamber 11B will be described below and the explanation of the second electron-beam irradiating devices 23 and 24 of the third sterilizing chamber 11C is omitted.

Based on the degree of vacuum of the vacuum chamber 30 in each of the first electron-beam irradiating devices 21 and 22, the sterilization controller 25 is set so as to reduce the electron beam output of the electron-beam irradiating device (e.g., 21) including the vacuum chamber 30 with a low degree of vacuum and increase the electron beam output of the electron-beam irradiating device 22 including an electron beam generator with a high degree of vacuum. This is because a decrease in the degree of vacuum of the vacuum chamber 30 is likely to cause sparking between the electrode 33 and the housing 31 grounded in the electron-beam irradiating device 21 (22 to 24), temporarily (for 0.1 to 0.2 seconds) stopping outputting electron beams. This may reduce an electron dose irradiated to the sterilization surface F of the container B and cause poor sterilization.

Moreover, the sterilization controller 25 controls the sum of electron beam outputs irradiated from the first electron-beam irradiating devices 21 and 22 so as to allows sterilization on the sterilization surface F of the container B.

In addition to the same effect as the first embodiment, the configuration of the second embodiment can considerably reduce the occurrence of sparking by lowering an electron beam output, though the vacuum chambers 30 of the electron-beam irradiating devices 21 to 24 decrease in degree of vacuum.

For example, if the sterilization equipment can treat (sterilize) 600 containers B per minute, each of the electron-beam irradiating devices 21 to 24 irradiates the container B with electron beams for 0.1 seconds. The container B is transported in 0.2 seconds from the first and second upstream electron-beam irradiating devices 21 and 23 to the first and second downstream electron-beam irradiating devices 22 and 24. The sterilization controller 25 has to adjust the outputs of the first and second downstream electron-beam irradiating devices 22 and 24 in 0.2 seconds.

In the second embodiment, an electron beam output is set based on a vacuum state in each of the vacuum chambers 30 of the electron-beam irradiating devices 21 to 24. The electron beam outputs of the upstream electron-beam irradiating devices 21 and 23 and the downstream electron-beam irradiating devices 22 and 24 may be set based on the operating times and conditions of the upstream electron-beam irradiating devices 21 and 23 and the downstream electron-beam irradiating devices 22 and 24.

For the sterilization surfaces F and R, the second shielded chamber 11B and the third shielded chamber 11C each include two of the first and second electron-beam irradiating devices 21 to 24. At least three electron-beam irradiating devices may be provided in each of the shielded chambers.

Having described the invention, the following is claimed:

1. A container sterilization method for sterilizing a container with electron beams irradiated from electron-beam irradiating devices while transporting the container along a carrier path, the method comprising:
    irradiating a portion of an outside surface of the container with electron beams irradiated from one or more upstream electron-beam irradiating devices and one or more downstream electron-beam irradiating devices spaced with respect to each other at a predetermined distance along the carrier path, wherein each of the one or more upstream and downstream electron-beam irradiating devices has a vacuum chamber;
    controlling a sum of electron beam outputs irradiated from the one or more upstream and downstream electron-beam irradiating devices by means of a sterilization controller so as to perform sterilization on the portion of the outside surface of the container;
    monitoring a vacuum state in the vacuum chamber of each of the one or more upstream and downstream electron-beam irradiating devices; and
    controlling an electron beam output of the one or more upstream and downstream electron-beam irradiating devices having the vacuum chamber with a low degree of vacuum to be smaller than an electron beam output of the one or more upstream and downstream electron-beam irradiating devices having the vacuum chamber with a high degree of vacuum, in order to prevent sparking in the one or more upstream and downstream electron-beam irradiating devices having the vacuum chamber with the low degree of vacuum.

2. The container sterilization method according to claim 1, when the electron beam output irradiated from the one or more upstream electron-beam irradiating devices changes from a set range, changing the electron beam output irradiated from the one or more downstream electron-beam irradiating devices so as to control the sum of the electron beam outputs from the one or more upstream and downstream electron-beam irradiating devices to be equal to or higher than a set value of an electron beam output that allows external sterilization on the container when the container is irradiated with the changed electron-beam output at the one or more upstream electron-beam irradiating devices transported to the one or more downstream electron-beam irradiating devices.

3. The container sterilization method according to claim 1, wherein the step of irradiating the portion of the outside surface comprises:
    irradiating a first portion of the outside surface with electron beams irradiated from respective first upstream and downstream electron-beam irradiating devices spaced with respect to each other at the predetermined distance along the carrier path; and
    irradiating a second portion of the outside surface with electron beams irradiated from respective second upstream and downstream electron-beam irradiating devices spaced with respect to each other at the predetermined distance along the carrier path;
    wherein the step of controlling comprises controlling the sum of electron beam outputs irradiated from each of the respective first and second upstream and downstream electron-beam irradiating devices so as to perform sterilization on the respective first and second portions of the outside surface of the container.

4. The container sterilization method according to claim 3, wherein the respective steps of irradiating the first and second portions of the outside surface comprise irradiating first and second substantially half sterilization surfaces of the outside surface that are symmetrical to each other on the container.

5. The container sterilization method according to claim 3, wherein the step of irradiating the first portion comprises transporting the container into a first shielded chamber and irradiating with the first upstream and downstream electron-beam irradiating devices located in the first shielded chamber, and wherein the step of irradiating the second portion comprises transporting the container into a second shielded chamber and irradiating with the second upstream and downstream electron-beam irradiating devices located in the second shielded chamber.

6. A container sterilization method for sterilizing a container with electron beams irradiated from electron-beam irradiating devices while transporting the container along a carrier path, the method comprising:
    irradiating a first portion of an outside surface of the container with an electron beam irradiated from an upstream electron-beam irradiating device having a vacuum chamber;
    irradiating a second portion of the outside surface of the container substantially identical to the first portion with an electron beam irradiated from a downstream electron-beam irradiating device having a vacuum chamber, wherein the upstream and downstream electron-beam irradiating devices are spaced with respect to each other at a predetermined distance along the carrier path;

controlling a sum of electron beam outputs irradiated from the upstream and downstream electron-beam irradiating devices by means of a sterilization controller so as to perform sterilization on the first and second portions of the outside surface of the container; and monitoring a vacuum state in the vacuum chamber of each of the upstream and downstream electron-beam irradiating devices; and controlling an electron beam output of the upstream and downstream electron-beam irradiating devices having the vacuum chamber with a low degree of vacuum to be smaller than an electron beam output of the upstream and downstream electron-beam irradiating devices having the vacuum chamber with a high degree of vacuum, in order to prevent sparking in the upstream and downstream electron-beam irradiating devices having the vacuum chamber with the low degree of vacuum.

* * * * *